US008551788B2

(12) United States Patent
Ingenhoven et al.

(10) Patent No.: US 8,551,788 B2
(45) Date of Patent: *Oct. 8, 2013

(54) METHOD FOR SELECTING PIPETTING PARAMETERS FOR A LIQUID

(71) Applicant: Tecan Trading AG, Mannedorf (CH)

(72) Inventors: Nikolaus Ingenhoven, Uerikon (CH); Robert Liebhard, Zurich (CH); Adi Zuppiger, Siebnen (CH); Werner Hälg, Mannedorf (CH)

(73) Assignee: Tecan Trading AG, Mannedorf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/736,658

(22) Filed: Jan. 8, 2013

(65) Prior Publication Data
US 2013/0126552 A1  May 23, 2013

Related U.S. Application Data

(63) Continuation of application No. 11/488,473, filed on Jul. 18, 2006, now Pat. No. 8,357,544.

(30) Foreign Application Priority Data

Jul. 22, 2005 (CH) ........................ 1223/05

(51) Int. Cl.
*G01N 1/10* (2006.01)

(52) U.S. Cl.
USPC ...... 436/180; 73/864.01; 73/19.05; 73/61.71; 141/275; 141/2; 436/47; 436/50; 422/504; 422/63; 422/534

(58) Field of Classification Search
USPC .................. 422/400; 436/43, 50, 47, 180
See application file for complete search history.

*Primary Examiner* — Sally Merkling
(74) *Attorney, Agent, or Firm* — Notaro, Michalos & Zaccaria P.C.

(57) ABSTRACT

A method of selecting pipetting parameters of a pipetting device for dispensing or pipetting a specific volume of a liquid sample, includes a fluid column of a fluid chamber of the pipetting device set into oscillation at the beginning of the aspiration, the pressure is monitored with the pressure transducer in the fluid chamber, and the pressure changes generated during aspiration into measuring signals are recorded. These measuring signals are processed by a computer or micro-processor and reproduced as a pressure curve, which is characteristic for the fluid column with the aspirated liquid sample, and which is compared with known pressure curves. Based on this comparison, pipetting parameters of the pipetting device are selected for the dispense or for pipetting a specific volume of the liquid sample. Selectable pipetting parameters include a speed of a movement of a pump piston of the pipetting device.

24 Claims, 12 Drawing Sheets

Fig. 8
Fig. 9
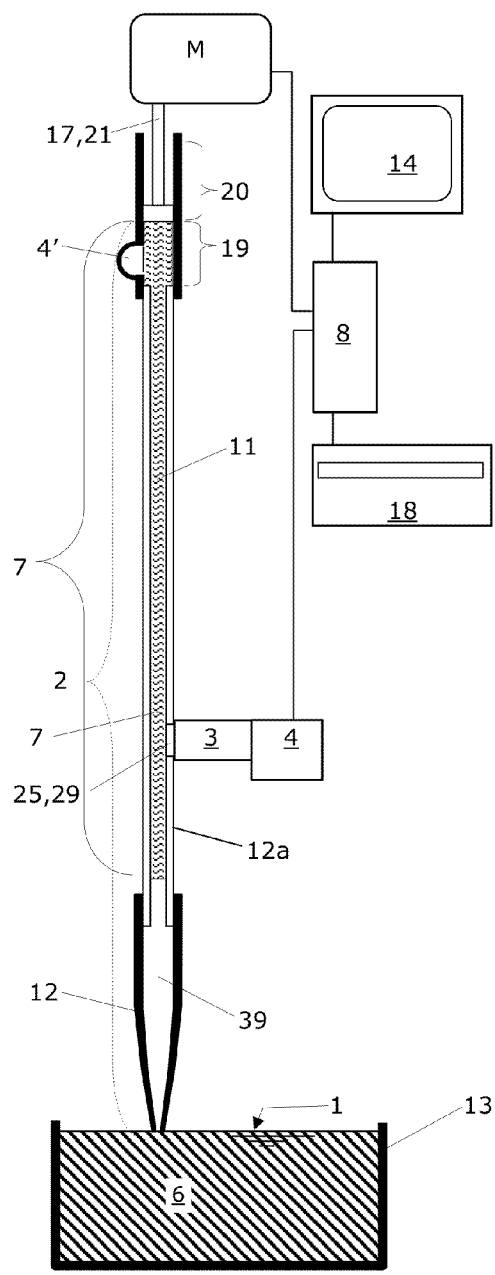
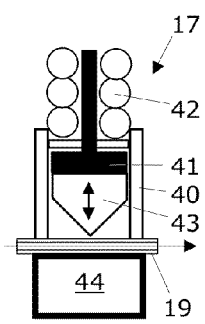

Fig. 10 H₂O
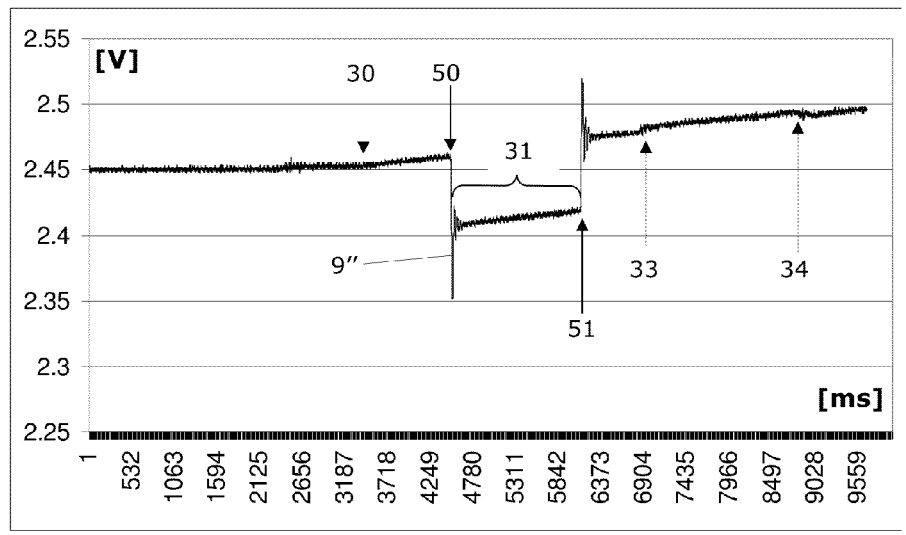
Fig. 11 H₂O
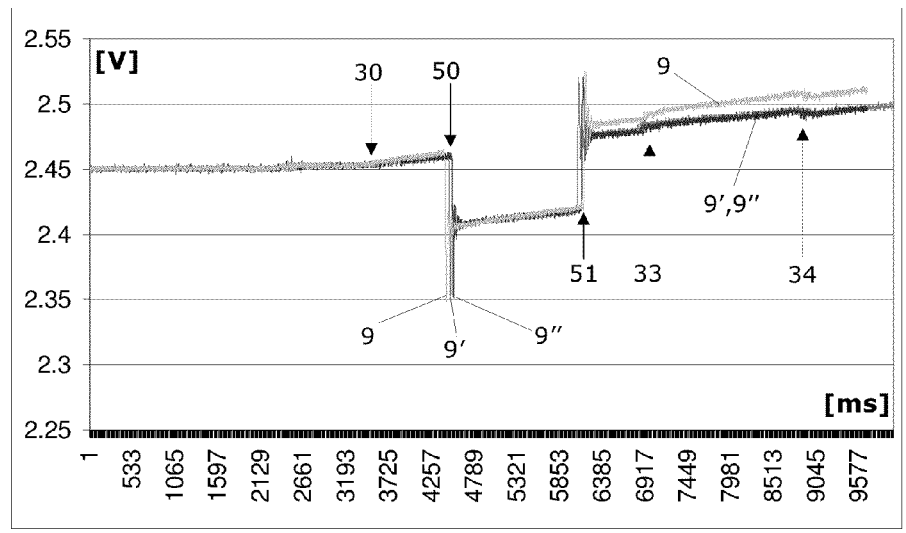

Fig. 12 H₂O/DMSO
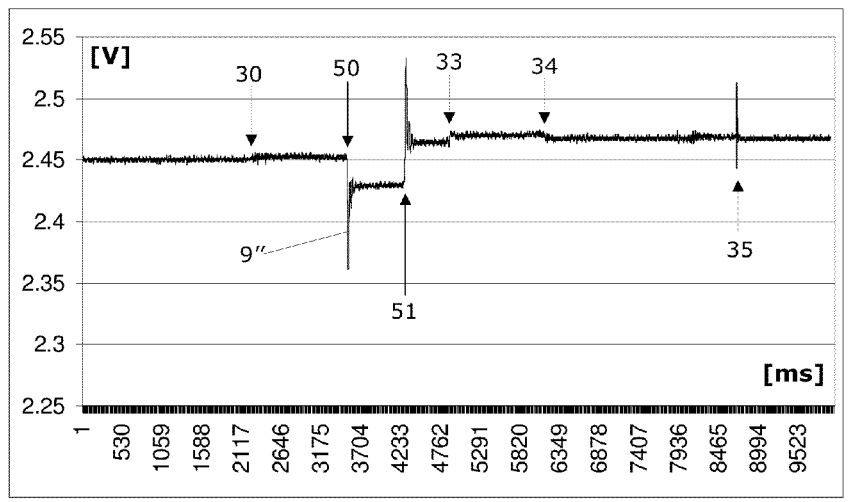
Fig. 13 H₂O/DMSO
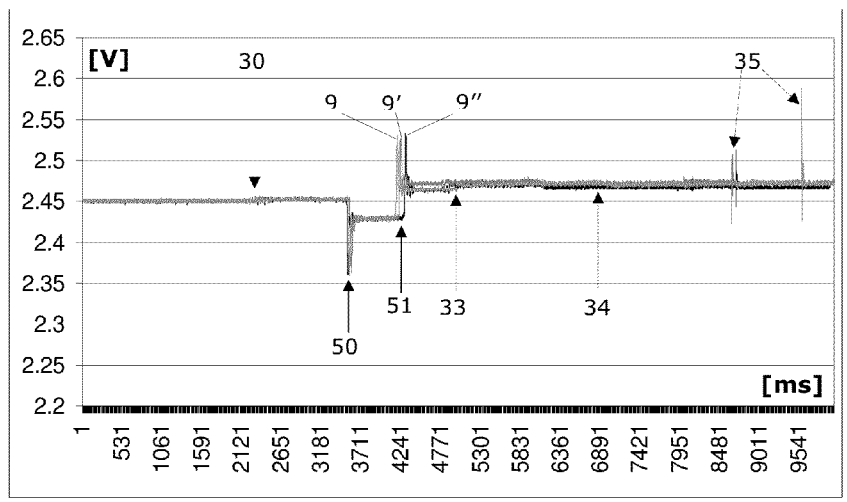

Fig. 14 DMSO
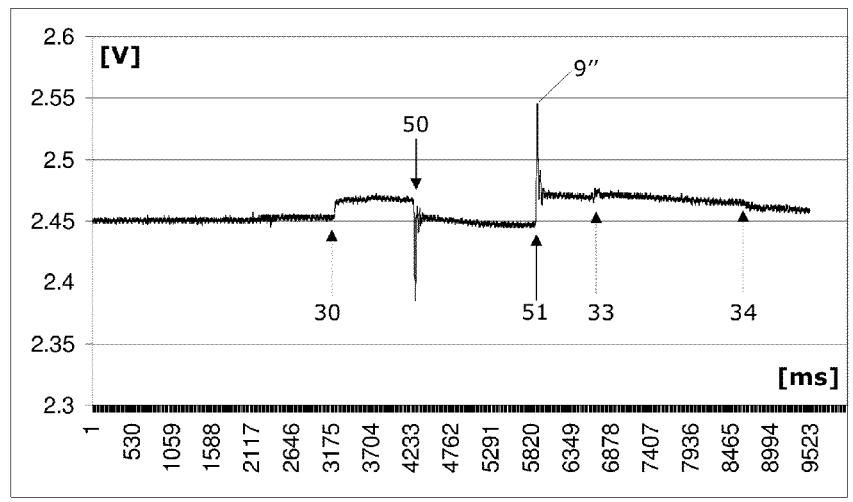
Fig. 15 DMSO
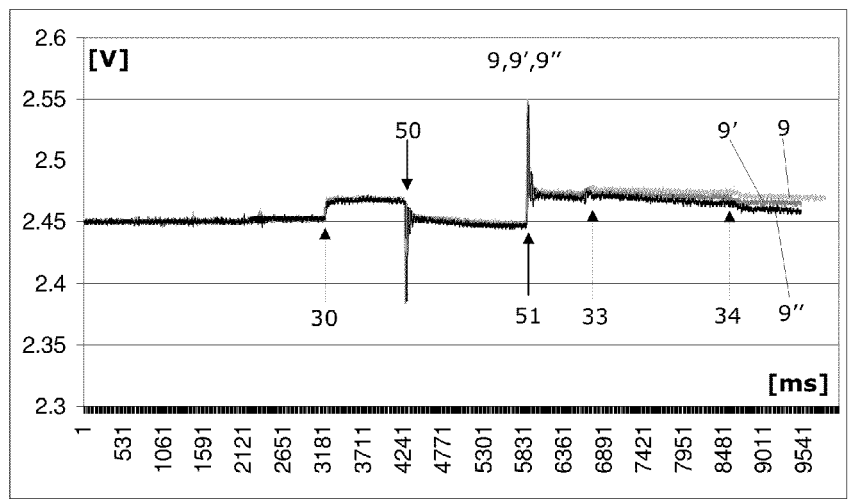

Fig. 16  H₂O/PEG
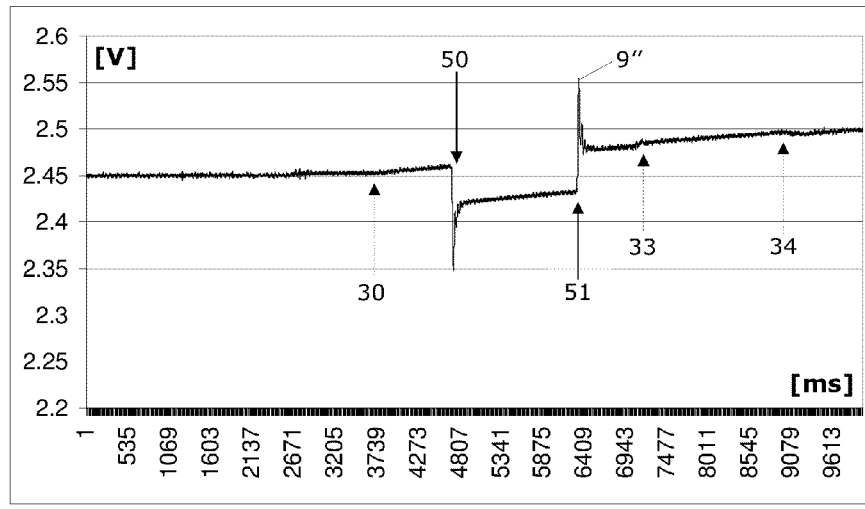
Fig. 17  H₂O/PEG
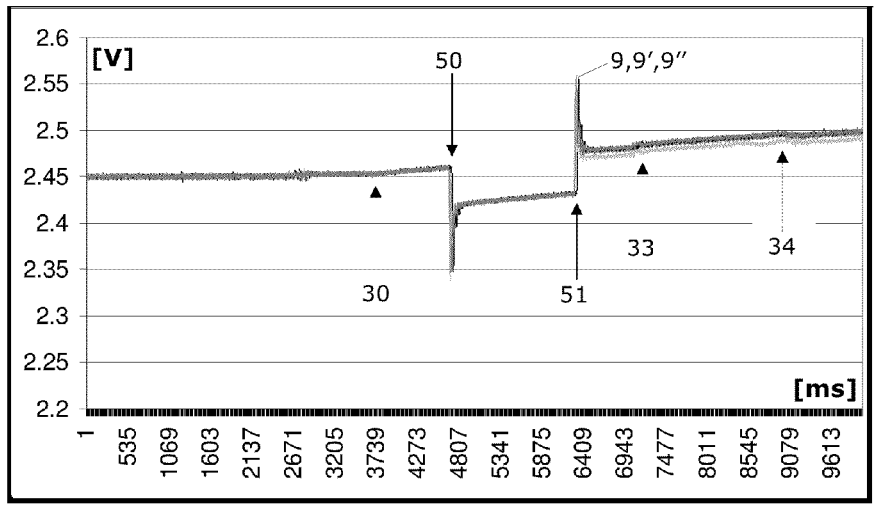

Fig. 18 Acetonitrile
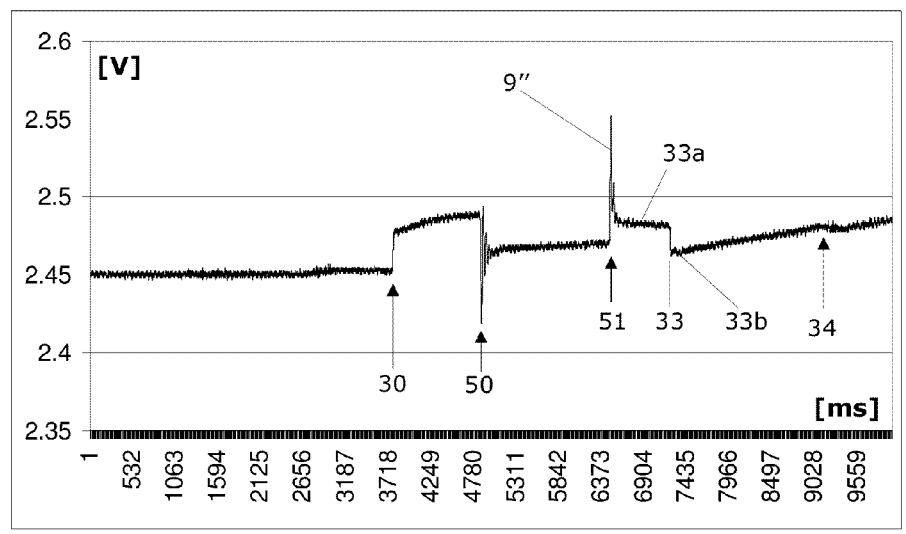
Fig. 19 Acetonitrile
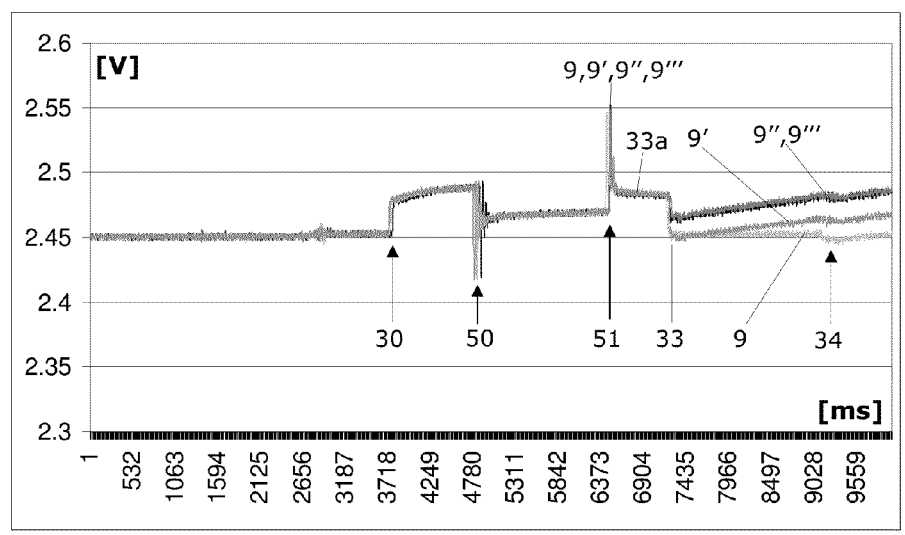

Fig. 20 Acetone
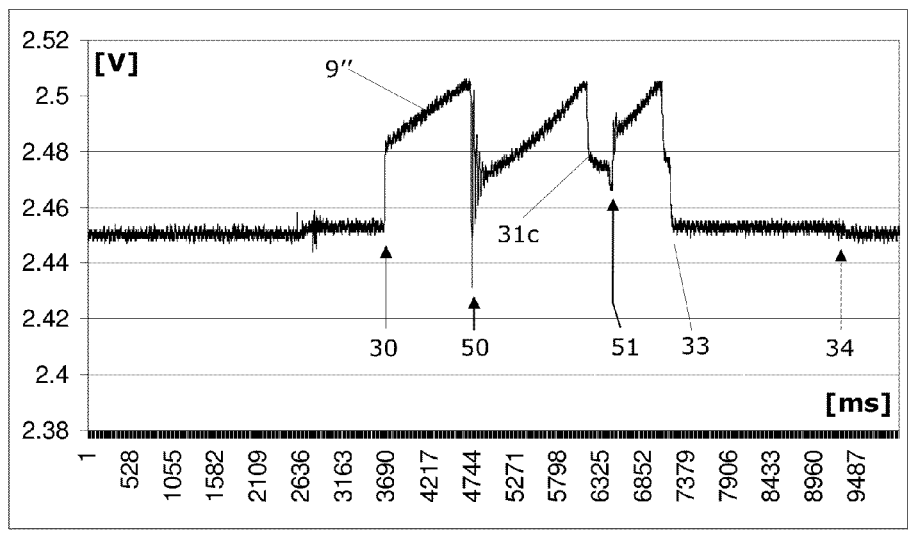
Fig. 21 Acetone
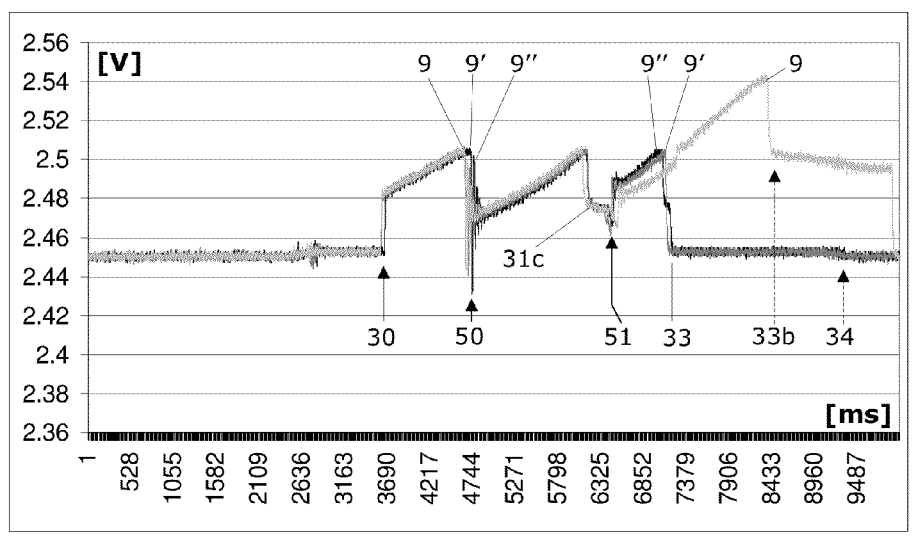

Fig. 22  H₂O
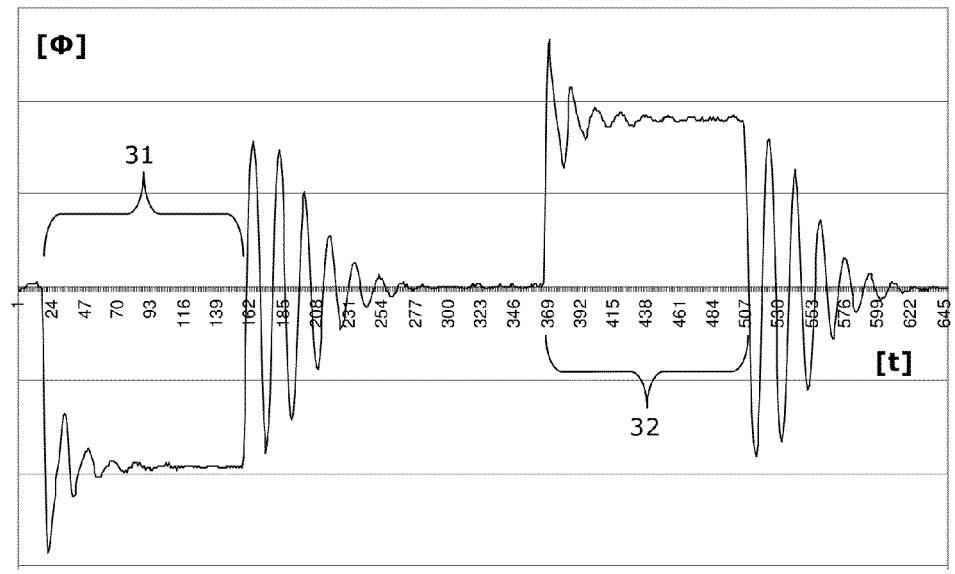
Fig. 23  Air
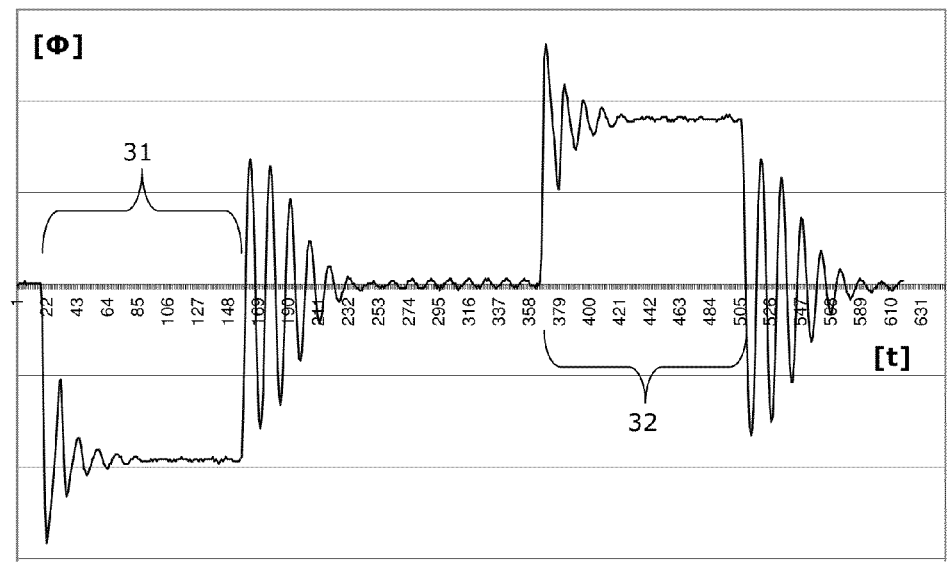

Fig. 24  H₂O and Air
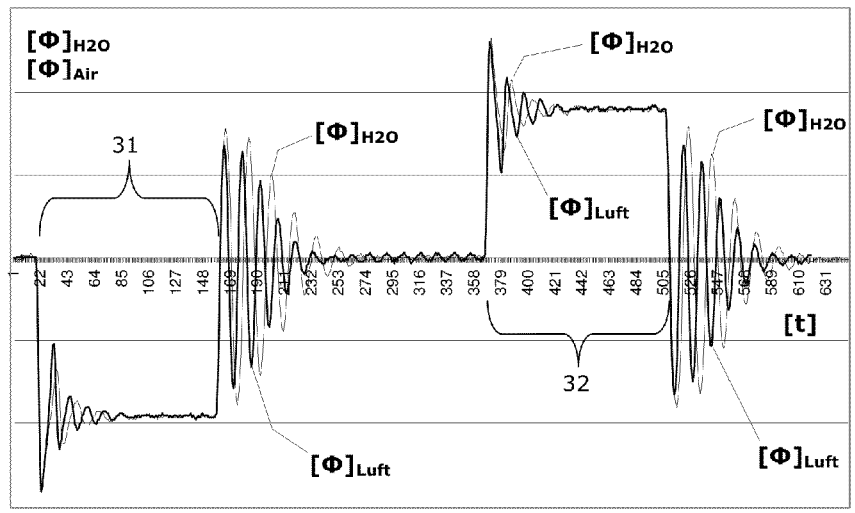
Fig. 25  H₂O minus Air
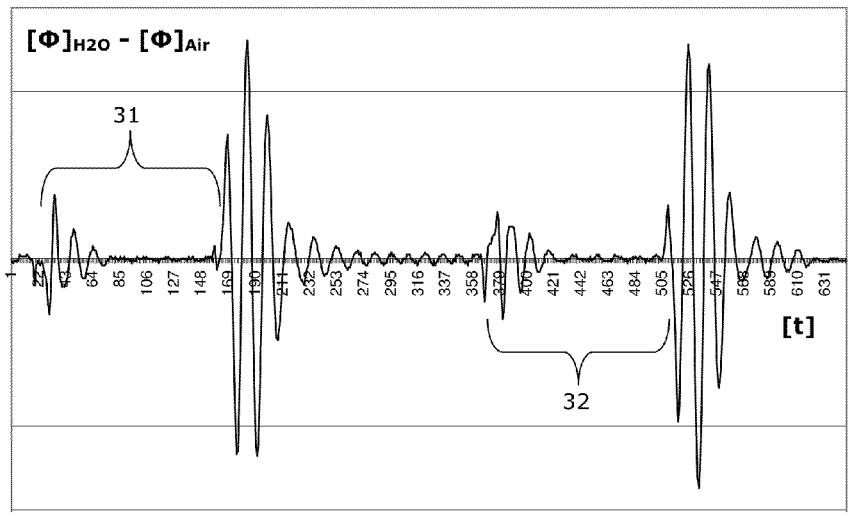

METHOD FOR SELECTING PIPETTING PARAMETERS FOR A LIQUID

CROSS-REFERENCE TO RELATED APPLICATIONS

This is a continuation of U.S. patent application Ser. No. 11/488,473, filed on Jul. 18, 2006, now U.S. Pat. No. 8,357,544, which claims priority on Swiss Patent Application No. CH 01223/05, filed on Jul. 22, 2005, which priority claim is repeated herein, and both of which are incorporated herein by reference.

FIELD AND BACKGROUND OF THE INVENTION

The present invention relates to a method for selecting pipetting parameters for a liquid, in which a fluid chamber is connected to a measuring chamber and the internal pressure of this measuring chamber is monitored using a pressure transducer, and in which at least a first part of this fluid chamber is brought into fluid connection with a sample of this liquid. Especially preferred embodiments of the method according to the present invention relate to a pipetting device for liquid handling of liquid samples.

The present invention thus comprises a method for selecting pipetting parameters for liquids in a pipetting device for aspirating and dispensing liquid volumes, such as samples, of human bodily fluids. Such a pipetting device comprises a pipette tip which is connected to a pump.

Industrial branches which are concerned, for example, with pharmaceutical research or clinical diagnostics using biochemical technologies require facilities for processing liquid volumes and liquid samples. Automated facilities typically comprise a single pipetting device or multiple pipetting devices which are used on liquid containers located on the worktable of a workstation. Such workstations are often capable of executing greatly varying work on these liquid samples, such as optical measurements, pipetting, washing, centrifuging, incubation, and filtration. One or more robots, which operate according to Cartesian or polar coordinates, may be used for sample processing at such a workstation. Such robots may carry and relocate liquid containers, such as sample tubes or microplates. Such robots may also be used as "robotic sample processors" (RSP), such as a pipetting device for aspirating and dispensing, or as a dispenser for distributing liquid samples. Preferably, such facilities are monitored and controlled by a computer. A decisive advantage of such facilities is that large numbers of liquid samples may be processed automatically over long time spans of hours and days without a human operator having to engage in the processing process.

Pipetting devices known from the prior art (cf., for example, U.S. Pat. No. 4,675,301, U.S. Pat. No. 4,794,085, and U.S. Pat. No. 5,723,795) comprise a pipette tip which is connected to a pump. Some of these devices comprise a fluid chamber, to which a pressure transducer having a pressure sensor is connected via a gas-filled chamber. This fluid chamber is defined by the pipette tip, a first line which connects the pipette tip to a pump, and an active part of this pump.

When pipetting liquids, the question of their type often arises, i.e., the physical features or constants of this liquid. Classifying liquids on the basis of their physical constants, such as surface tension, viscosity, or vapor pressure, is therefore known from the prior art. The suitable pipetting parameters may then be determined on the basis of the corresponding classification and these liquids may be pipetted with improved precision.

Measuring the viscosity of a liquid sample using a pipetting device is known from EP 0 608 425. In this case, one proceeds from a time span which is required to change a defined, original partial vacuum applied via a pipette tip used for aspirating the liquid by a specific amount. This time value is compared to known viscosity data related to such time values in a table and the current viscosity of the liquid is thus ascertained. When this method is applied, with centrifuged blood samples, the remaining fraction having the red blood cells may be collected separately from the blood plasma.

However, as explained above, other parameters also play a significant role in pipetting. Thus, because of the differing vapor pressures, it is known that samples of water or acetone must be pipetted in completely different ways. The surface tension of these solvents also differs greatly. The viscosity, the vapor pressure, and the surface tension are specified for several typical solvents in Table 1 as an illustration.

TABLE 1

| Solvent (at 20° C.) | Viscosity [mPas] | Vapor pressure [hPa] | Surface tension [mN/m] |
|---|---|---|---|
| Water | 1.002 | 23 | 72.8 |
| DMSO | 2.14 | 0.56 | 43.0 |
| Acetone | 0.32 | 240 | 23.3 |
| Ethanol | 1.2 | 59 | 22.3 |

It is obvious from Table 1 that the surface tensions of acetone and ethanol are very similar. Nonetheless, these two solvents are not to be treated identically during pipetting because of the very different values of their parameters of viscosity and/or vapor pressure. It is thus obvious that it hardly suffices to determine only one parameter in order to be able to automatically and reliably pipette such different solvents, which are used routinely in all biochemical laboratories. Detecting all of these parameters (and possibly even further parameters such as the wettability of the pipette tip as a function of the liquid to be pipetted and/or the material used for the pipette tip) would require too much machine and time outlay, however. This is true above all when, in case of an automated workstation, the throughput of hundreds or thousands of samples within the shortest possible time must be ensured. This is certainly made more difficult if the solvents and/or liquid samples are unknown compositions having unknown physical parameters, which must also be pipetted automatically as much as possible.

SUMMARY OF THE INVENTION

The present invention is thus based on the object of suggesting an alternative method, using which pipetting parameters for liquid samples may easily be selected and the liquid samples pipetted as needed.

This object is achieved, for example, in that a method is suggested, in which a fluid chamber is connected to a measuring chamber and the internal pressure of this measuring chamber is monitored using a pressure transducer, and in which at least a first part of this fluid chamber is brought into fluid connection with a sample of this liquid. The method according to the present invention is characterized in this case in that pressure changes are generated in a fluid column, which is situated in the fluid chamber and is essentially coherent, these pressure changes causing corresponding pressure changes in the measuring chamber pneumatically connected to the fluid column, which are recorded by the pressure transducer and converted into measuring signals, these measuring signals being processed by a computer and reproduced as a pressure curve, and the course of this pressure curve being compared to the course of known pressure curves.

In fact—in a type of "approximation of the experience of an experimenter"—it is summarily established how the liquid behaves in a known pipetting system. This was explained above by detecting the change of the pipette internal pressure. According to the present invention, this method may already be performed upon immersion in a liquid to be pipetted or during aspiration of this liquid.

Further parameters selected according to the present invention, which result in comparable results, comprise detecting the changes of this selected parameter during aspiration of the liquid to be pipetted in the form of:
- the current flow of the system liquid or the liquid to be pipetted in a pipette;
- the total weight of a container from which a liquid to be pipetted is aspirated;
- the power consumption of a DC motor which is used to move the pump piston during aspiration of the liquid to be pipetted;
- the power consumption of the piezo drive of a micro-diaphragm pump which is used during aspiration of the liquid to be pipetted to generate a partial vacuum in the pipette tip.

This object is achieved by a method for selecting pipetting parameters for a liquid in a known pipetting system for this liquid. The method being characterized in that pressure changes during immersion and aspiration are detected as a pressure curve typical for this liquid; that this pressure curve is compared to corresponding pressure curves of known liquids, and that pipetting parameters for this liquid are selected on the basis of this comparison.

Additional, preferred features according to the present invention result from the dependent claims.

Such a liquid may subsequently be pipetted correctly, i.e., dispensed using a pipette in a specific quantity and/or in a specific volume into a container, e.g., a well of a microplate. For this purpose, a parameter set for the activation of the pipetting device to dispense liquid samples is selected. The selection is performed manually or automatically in that the parameter set which comes closest to the set requirements is selected from a library of parameter sets on the basis of fixed tolerance ranges.

BRIEF DESCRIPTION OF THE DRAWINGS

The method according to the present invention will now be explained in detail on the basis of schematic figures of exemplary embodiments, which do not restrict the scope of the present invention.

FIG. 8 shows a vertical section through a device or system capable of performing the method according to the present invention, according to a third embodiment having a motorized piston pump;

FIG. 9 shows a partial section through an electromechanical variation of an alternative, pump-independent pulse unit, using which pressure changes may be generated in the fluid chamber;

FIG. 10 shows the course of a typical pressure curve for water as the sample liquid;

FIG. 11 shows an approximate superposition of three individual pressure curves achieved using water;

FIG. 12 shows the course of a typical pressure curve for a water/DMSO mixture as the sample liquid;

FIG. 13 shows an approximate superposition of three individual pressure curves achieved using the water/DMSO mixture (1:1);

FIG. 14 shows the course of a typical pressure curve for DMSO as the sample liquid;

FIG. 15 shows an approximate superposition of three individual pressure curves achieved using DMSO;

FIG. 16 shows the course of a typical pressure curve for a water/PEG mixture (7% PEG in water) as the sample liquid;

FIG. 17 shows an approximate superposition of three individual pressure curves achieved using the water/PEG mixture;

FIG. 18 shows the course of a typical pressure curve for acetonitrile as the sample liquid;

FIG. 19 shows an approximate superposition of four individual pressure curves achieved using acetonitrile;

FIG. 20 shows the course of a typical pressure curve for acetone as the sample liquid; and FIG. 21 shows an approximate superposition of four individual pressure curves achieved using acetone.

FIG. 22 shows flow changes in the pipette of a pipetting device or pipetting system capable of performing the method according to the present invention during aspiration and dispensing of a water sample;

FIG. 23 shows flow changes in the pipette of a pipetting device or pipetting system capable of performing the method according to the present invention during aspiration and dispensing of an air sample;

FIG. 24 shows a superposition of the flow change curves of FIG. 22 "water" and FIG. 23 "air";

FIG. 25 shows a subtraction illustration of the flow change curves FIG. 22 "water" minus FIG. 23 "air";

DETAILED DESCRIPTION OF THE INVENTION

Figure 1:
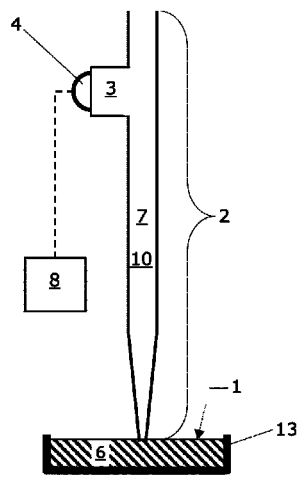
FIG. 1 shows a vertical section through a device or system capable of performing the method according to the present invention, according to a first embodiment and according to a first use.

FIG. 1 shows a vertical section through a device or system capable of performing the method according to the present invention, according to a first embodiment and according to a first use. This device comprises a fluid chamber 2, which is connected to a measuring chamber 3. This connection is implemented here as a direct, open passage between the two chambers 2,3. The internal pressure of the measuring chamber 3 is monitored using a pressure transducer 4, which is connected to a computer or microprocessor 8. In an alternative embodiment, the pressure transducer may be connected directly to the fluid chamber (cf. FIG. 2). A first part 5 of the fluid chamber, which comprises the entire fluid chamber 2 of a pipette or pipette tip here, is filled with a gas in this case. The pipette tip contacts the surface of a liquid 1, which is provided as a sample 6 in a container 13. Such containers may have any arbitrary form and content and are implemented, for example, as sample tubes, wells of a microplate, troughs, or Petri dishes. Upon immersion of the pipette tip in the sample liquid 6, the fluid column 7, which is formed entirely by gas here, experiences pressure changes and/or pressure oscillations.

Figure 2:
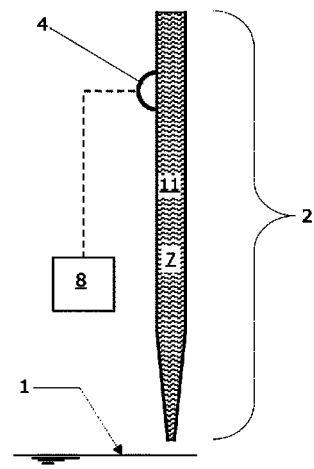
FIG. 2 shows a vertical section through a device or system capable of performing the method according to the present invention, according to a second embodiment and according to a second use.

FIG. 2 shows a vertical section through a device or system capable of performing the method according to the present invention, according to a second embodiment and according to a second use. This device comprises a fluid chamber 2, which is connected to a measuring chamber 3. Actually, the fluid chamber 2 simultaneously also forms the measuring chamber 3 here. The internal pressure of the measuring chamber 3 is monitored using a pressure transducer 4, which is connected to a computer or microprocessor 8. The fluid chamber 2 of a pipette or pipette tip contacts the surface of a liquid 1. Upon immersion of the pipette tip in the liquid 1, the fluid column 7, which is formed entirely by a system liquid 11 here, experiences pressure changes and/or pressure oscillations.

Figure 3:
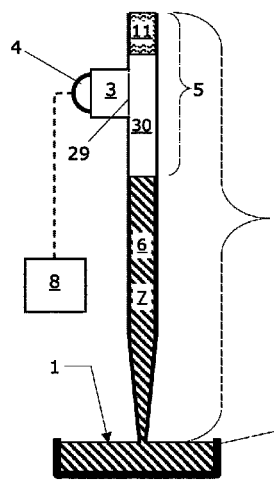
FIG. 3 shows a vertical section through a device or system capable of performing the method according to the present invention, according to a third embodiment and according to a third use.

FIG. 3 shows a vertical section through a device or system capable of performing the method according to the present invention, according to a third embodiment and according to a third use. This device comprises a fluid chamber 2, which is connected to a measuring chamber 3. This connection is implemented here as a flexible diaphragm 29, which is situated between the two chambers 2,3 to form a seal. The internal pressure of the measuring chamber 3 is monitored using a pressure transducer 4 which is connected to a computer or microprocessor 8. A first part 5 of the fluid chamber, which only comprises the lower part of the fluid chamber 2 of a pipette or pipette tip here, is filled in this case with an air gap 39 and with system liquid 11. The system liquid 11 may also be left out here. Preferably, above all in the first embodiment (cf. FIG. 1), in which this connection is implemented as a direct, open passage between the two chambers 2,3, the air gap 39 is situated in the region of the measuring chamber 3. In the embodiment provided here, however, this is not required, because the diaphragm 29 protects the measuring chamber 3 from penetrating sample or system liquid. The pipette tip is immersed somewhat in the liquid 1 and sample liquid 6 has already been drawn into the pipette tip. When sample liquid 6 is drawn or aspirated, the fluid column 7, which comprises sample liquid 6, a gas, and possibly system liquid 11 here, experiences pressure changes and/or pressure oscillations.

Figure 4:
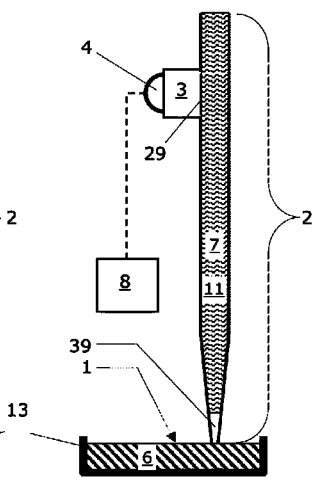
FIG. 4 shows a vertical section through a device or system capable of performing the method according to the present invention, according to a third embodiment and according to a fourth use.

FIG. 4 shows a vertical section through a device or system capable of performing the method according to the present invention, according to a third embodiment and according to a fourth use. This device is implemented identically to that shown in FIG. 3. The entire fluid chamber 2 of a pipette or pipette tip is filled here in the area of the tip with an air gap 39 and otherwise with system liquid 11. In the embodiment provided here, the diaphragm 29 protects the measuring chamber 3 from penetrating system liquid 11. The pipette tip is immersed somewhat in the liquid 1. Upon immersion of sample liquid 6, the fluid column 7, which comprises a gas and system liquid 11 here, experiences pressure changes and/or pressure oscillations.

Figure 5:
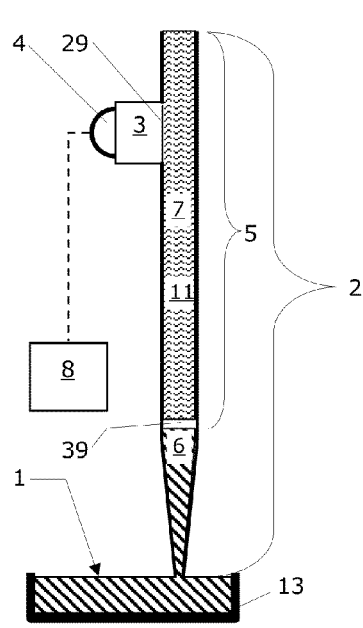
FIG. 5 shows a vertical section through a device or system capable of performing the method according to the present invention, according to a third embodiment and according to a fifth use.

FIG. 5 shows a vertical section through a device or system capable of performing the method according to the present invention, according to a preferred third embodiment and according to a fifth use. This device is implemented identically to that shown in FIGS. 3 and 4. The entire fluid chamber 2 of a pipette or pipette tip is already filled here in the area of the tip with sample liquid 6, which is separated using a small air gap 39 from the system liquid 11. In the embodiment provided here, the diaphragm 29 protects the measuring chamber 3 from penetrating system liquid 11. The measuring chamber 3 may be filled with a gas (e.g., air or $N_2$). If the measuring chamber is filled with a liquid (e.g., oil, water), it may additionally comprise a gas bubble which separates the sensor from the liquid. The pipette tip is still immersed somewhat in the liquid 1. Upon aspiration of sample liquid 6, the fluid column 7, which comprises a gas and system liquid 11 here, experiences pressure changes and/or pressure oscillations.

In FIGS. 1 through 5 described up to this point, the pipette is connected via a line to a pump (both not shown). Such pumps may be selected arbitrarily and are implemented for delivering larger volumes in the range of microliters or smaller volumes in the range of nanoliters to picoliters. The pressure changes described also cause pressure changes in the measuring chamber 3 pneumatically connected to the fluid column 7, which are recorded by the pressure transducer 4 and converted into measuring signals. These measuring signals are processed by the computer or microprocessor 8 and reproduced as a pressure curve 9 (cf., for example, FIG. 7). The course of this pressure curve 9 may then be compared to the course of known pressure curves. Because each of these pressure curves is characteristic for a specific sample liquid 6, for the currently provided liquid 1 there may be selected pipetting parameters on the basis of this comparison. An essential advantage of the present invention is thus based on the fact that through a single test and a single comparison, a previously unknown sample liquid may be characterized and pipetting parameters assigned without many individual parameters of this sample liquid having to be determined in correspondingly many experiments.

Figure 6:
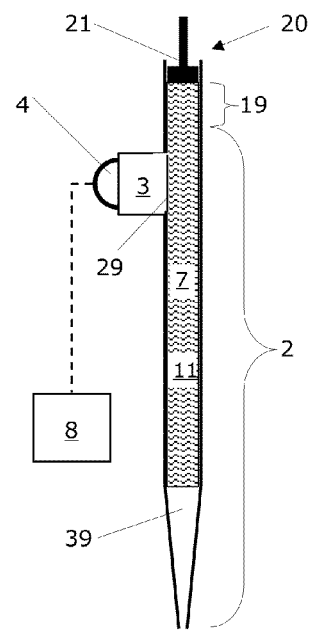
FIG. 6 shows a vertical section through a device or system capable of performing the method according to the present invention, according to a third embodiment having a piston pump.

FIG. 6 shows a vertical section through a device or system capable of performing the method according to the present invention, according to a third embodiment having a piston pump. The embodiment and the use correspond to those which were described in connection with FIG. 4. The fluid column 7, which comprises an air gap 39 in the area of the pipette tip, is essentially formed by the system liquid 11 here. Through a longer or shorter first line 19, depending on the construction of the device, which is also filled with system liquid, the fluid column 7 is extended up to the piston 21 of a piston pump 20. This piston pump 20 is used for generating a partial vacuum in the fluid chamber 2 for aspirating liquid samples 6 and for generating an overpressure in the fluid chamber 2 for dispensing liquid samples 6. This piston pump 20 is additionally used as a pulse unit 17, using which the essentially homogeneous fluid column 7, which extends up to the air gap 39, may be caused to oscillate. The diaphragm 29 protects the measuring chamber 3 from penetrating system liquid. The pipette tip is at a distance from a sample liquid 6 at the moment, so that the situation shown here occurs when the pipette tip is prepared for sample aspiration using system liquid and an air gap. In this phase, the pressure transducer 4 is used for the detection of any gas bubbles in the fluid column, which may be discovered through characteristic changes in the pressure oscillations caused by the pulse unit 17.

For devices, i.e., pipetting devices which are especially well suited for performing the method according to the present invention, the applicant of the present patent application has submitted a priority application with the United States Patent and Trademark Office (USPTO) on Dec. 10, 2004 under number U.S. Ser. No. 11/009,247. These pipetting devices described in the priority application just cited differ from the known art in that they comprise, in addition to the features already cited in connection with U.S. Pat. No. 4,675,301, U.S. Pat. No. 4,794,085, and U.S. Pat. No. 5,723,795, a pulse generating unit, which is operationally linked to the liquid column located inside the fluid chamber. The pulse generating unit is implemented so that it causes a vertical movement of the liquid column, which in turn causes pressure differences in the gas chamber which is pneumatically connected to the fluid chamber. These pressure differences are detected by the pressure sensor and delivered by the pressure transducer in the form of corresponding signals to a computer connected thereto. On the basis of the data then provided by the computer, reaching a liquid surface in a container ("liquid level detection"), the presence of gas bubbles in the system liquid located in the fluid chamber, and/or the presence or absence of a filter in the pipette tip may be concluded. Especially preferred embodiments of a pipetting device according to U.S. Ser. No. 11/009,247, which herein is incorporated in its entirety, for use in performing the method according to the present invention are shown here in FIGS. 8 and/or 9.

In principle, all sudden or abrupt movements of the part of the pipetting device containing the fluid column 7 generate pressure changes in the measuring chamber 3 of a pipetting device or pipetting system capable of performing the method according to the present invention. Such pressure changes may occur as individual pressure spikes or as pressure oscillations, for example, a characteristic oscillation behavior being able to be assigned to every specific fluid column 7.

Figure 7:
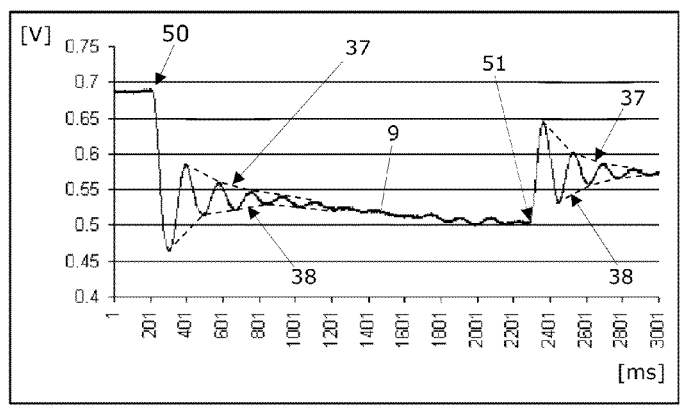
FIG. 7 shows pressure changes in the measuring chamber of a pipetting device or pipetting system capable of performing the method according to the present invention, which may be generated by oscillation behavior (here for water) characteristic for a specific fluid column.

FIG. 7 shows a pressure curve 9, in which the measured pressure values (in volts) are plotted against a time axis (in milliseconds). The pressure curve 9 displays characteristic pressure changes, which have been generated in this case in a fluid column filled with water as the system liquid 11. The sample liquid 6 was also water which was separated by an air gap 39 from the system liquid 11 (cf. embodiment without diaphragm 29 shown in FIG. 1, but use shown in FIG. 3). The beginning of the aspiration, upon which the piston 21 of the pump 20 was set in motion, is identified by 50. This sudden, single-side pulse which is delivered to the fluid column generates an oscillation of the fluid column which is detected as pressure changes in the measuring chamber 3. The end of the aspiration is identified by 51. This sudden pulse directed against the opposite side, which is delivered to the fluid column, again generates an oscillation of the fluid column which is also detected as pressure changes in the measuring chamber 3. The particular course shown of the upper and lower envelope curves 37,38 of the pressure curve 9 is characteristic for water. The aspiration over a time of approximately two seconds caused a pressure drop by a value corresponding to approximately 0.2 V.

FIG. 8 shows a vertical section through a pipetting device. This device or system capable of performing the method according to the present invention according to the third embodiment comprises a piston pump 20 (cf. FIG. 6). This pump is preferably a "CAVRO XP3000 plus Modular Digital Pump" (Tecan Systems Inc., 2450 Zanker Road, San Jose, Calif. 95138, USA) or a bellows pump, as is known, for example, from U.S. Pat. No. 5,638,986. The piston 21 is driven by the motor M. This device additionally comprises a disposable pipette tip 12 known per se, which is plugged onto a tubular pipette containing the fluid column 7. The pipette tip 12 is attached to a holder 12a. The fluid column 7 is formed by a system liquid 11. The fluid chamber 2 extends from the active parts of the pump, i.e., from the piston 21, via a line 19 implemented in accordance with the device requirements, the fluid column 2, and an air gap 39 up to the tip of the pipette tip 12. The entire disposable pipette tip 12 is filled with a gas (typically air) and is slightly immersed in a liquid sample 6, which is located in a container 13. The immersion of the pipette tip 12 in the sample liquid 6 causes pressure changes and/or pressure oscillations in the fluid column 7. These pressure changes also cause pressure changes in the measuring chamber 3 pneumatically connected to the fluid column 7 (preferably separated by a flexible diaphragm 29), which are recorded by the pressure transducer 4 and converted into measuring signals. These measuring signals are processed by the computer or microprocessor 8 and reproduced as a pressure curve 9 (cf., for example, FIG. 7) on the display screen 14 or the printer 18 and may thus be displayed to an operator. This first pressure curve shows the penetration of the pipette tip 12 into the liquid 1 and thus represents a means for detecting the liquid surface 1 (=liquid level detection). This is thus detection of a liquid surface using pressure measurement. Such detection is therefore independent of whether or not the liquid 1 to be aspirated is electrically conductive. The device is thus ready to begin the aspiration process. This device preferably comprises an additional pressure transducer 4' in the area of the line 19, which connects the pipette to the piston pump 20 as "tubing". This additional pressure transducer 4' is preferably also connected to the computer or microprocessor 8 (not shown). Alternative pipette tips comprise the disposable tips shown made of inert plastic material, e.g., made of cost-effective polypropylene. Steel needles (with or without tips coated with titanium, platinum, or Teflon derivatives, for example) are also usable and are then preferably used as permanently installed, nondisposable pipette tips.

FIG. 9 shows a partial section through an electromechanical variation of an alternative, pump-independent pulse unit 17, using which pressure changes may also be generated in the fluid chamber 2. The line 19 is guided through a cylinder 40. A piston 41 having a wedge 43, which is movable essentially perpendicularly against the closed surface of the line 19, is situated in the interior of this cylinder 40. The wedge 43 is preferably made of soft plastic material and/or has a rounded edge so that the line 19 is not damaged. Other forms may also be selected for the wedge 43, such as balls or bodies having planar or curved faces. A preferably fixed floor 44 terminates the cylinder 40 on the side diametrically opposite the piston 41. This movement reversibly deforms the line 19, which triggers the cited pulse. Individual pulses or also pulse series may be triggered, so that the fluid column may be moved only briefly or set into oscillation. This pulse unit may preferably be operated independently of the movement of the pipette in the X, Y, or Z direction and independently of the operation of the pump 20. This pulse unit 17 supports in a preferred way the detection of gas bubbles in the system liquid 11, which is located in the fluid chamber 2. A coil 42 is used as the drive, for example.

EXAMPLES

All of the figures described in the following show a pressure curve 9 or multiple pressure curves 9,9',9", in which the measured pressure values (in volts) are plotted against a time axis (in milliseconds). In all cases, the pressure curves were generated in a fluid column filled with water as the system liquid 11. The sample liquid 6 was separated in all cases by an air gap 39 from the system liquid 11 (cf. FIG. 3). In all FIGS. 10 through 25, the essential procedures are identified by identical reference numerals as follows:

| | |
|---|---|
| 30 | immersion of the pipette tip in the sample liquid |
| 31 | aspiration/31c ejection of a bubble |
| 32 | dispensing |
| 33 | beginning of withdrawal of the pipette tip from the sample liquid 33a intermediate level/33b turning point |
| 34 | end of withdrawal of the pipette tip from the sample liquid |
| 35 | interference signals due to further travel movements, or disposal of pipette tip |
| 50 | beginning of the aspiration |
| 51 | end of the aspiration |

The aspiration of sample liquid 6 occurs in 10 steps after the immersion in the liquid 1 having a calculated flow velocity of 180 µl/second and during a time span of approximately 2 seconds.

FIG. 10 shows a single characteristic pressure curve 9''' for the sample liquid water. The pressure in the pipette, i.e., in the fluid chamber 2 and thus in the measuring chamber 3, rises slowly and continuously after the immersion 30, which may be attributed to a capillary effect of the pipette tip and thus the water penetrating therein. At the beginning 50 of the aspiration, the pressure first falls around 0.1 V and then oscillates symmetrically around a pressure lowered by approximately 0.05 V. At the end 51 of aspiration, the pressure first rises by 0.1 V and then oscillates symmetrically again around a pressure higher by approximately 0.05 V. At the beginning 33 of the withdrawal of the pipette tip from the sample liquid, the pressure rises only insignificantly and falls at the end 34 of the withdrawal of the pipette from the sample liquid by approximately the same absolute value. It is noticeable that the initially noted, continuous pressure increase continues with identical slope between the end points of the activities described.

FIG. 11 shows three characteristic pressure curves 9,9',9" for the sample liquid water. The high reproducibility of the results is obvious.

FIG. 12 shows a single characteristic pressure curve 9''' for a sample liquid having a water/DMSO mixture. The ratio of water to dimethyl sulfoxide is 1:1. The pressure in the pipette, i.e., in the fluid chamber 2 and thus in the measuring chamber 3 does not rise significantly from the immersion 30. At the beginning 50 of the aspiration, the pressure first falls by 0.08 V and then oscillates asymmetrically around a pressure lowered by approximately 0.025 V. At the end 51 of the aspiration, the pressure first rises by 0.1 V and then again oscillates asymmetrically around a pressure higher by approximately 0.015 V. At the beginning 33 of the withdrawal of the pipette tip from the sample liquid, the pressure rises only insignificantly and falls at the end 34 of the withdrawal of the pipette tip from the sample liquid by approximately the same absolute value. It is noticeable that the pressure between the end points of the activities described is constant.

FIG. 13 shows three characteristic pressure curves 9,9',9" for the sample liquid having the water/DMSO mixture in the ratio 1:1. The high reproducibility of the results is obvious. The greatest variation relates to the instant of the replacement 35 of the pipette tip.

FIG. 14 shows a single characteristic pressure curve 9''' for the sample liquid DMSO. The pressure in the pipette, i.e., in the fluid chamber 2 and thus in the measuring chamber 3, rises noticeably from the immersion 30 by 0.015 V. At the beginning 50 of the aspiration, the pressure first drops by 0.066 V and then oscillates symmetrically approximately around the starting pressure. At the end 51 of aspiration, the pressure first rises by 0.1 V and then oscillates asymmetrically around a pressure higher by approximately 0.02 V. At the beginning 33 of the withdrawal of the pipette tip from the sample liquid, the pressure rises only insignificantly and falls at the end 34 of the withdrawal the pipette tip from the sample liquid by approximately the same absolute value. It is noticeable that the pressure between end points of the activities described is constant, but drops slightly with differing slope multiple times.

FIG. 15 shows three characteristic pressure curves 9,9',9" for the sample liquid DMSO. The high reproducibility of the results is obvious.

FIG. 16 shows a single characteristic pressure curve 9''' for sample liquid having a water/polyethylene glycol mixture (7% PEG in water). The pressure in the pipette, i.e., in the fluid chamber 2 and thus in the measuring chamber 3, rises slowly and continuously from the immersion 30, which may be attributed to a capillary effect of the pipette tip and thus water/PEG mixture penetrating therein. At the beginning 50 of the aspiration, the pressure first falls by 0.11 V and then oscillates extremely asymmetrically around a pressure lowered by approximately 0.037 V. At the end 51 of aspiration, the pressure first rises by 0.13 V and then again oscillates extremely asymmetrically around a pressure higher by approximately 0.037 V. At the beginning 33 of the withdrawal of the pipette tip from the sample liquid, the pressure rises only insignificantly and falls at the end 34 of the withdrawal of the pipette tip from the sample liquid by approximately the same absolute value. It is noticeable that the initially noted, continuous pressure increase continues with identical slope between the end points of the activities described.

FIG. 17 shows three characteristic pressure curves 9,9',9" for the sample liquid having the water/PEG mixture (7% PEG in water). The high reproducibility of the results is obvious.

FIG. 18 shows a single characteristic pressure curve 9''' for the sample liquid acetonitrile. The pressure in the pipette, i.e., in the fluid chamber 2 and thus in the measuring chamber 3, rises rapidly from the immersion 30 by 0.027 V and rises more slowly to a pressure elevated by approximately 0.04 V. At the beginning 50 of the aspiration, the pressure first falls by 0.09 V and then oscillates nearly symmetrically around a pressure lowered by only approximately 0.02 V. At the end 51 of aspiration, the pressure rises very steeply by 0.08 V and oscillates extremely lopsidedly around an intermediate level 33a higher by only approximately 0.035 V. The pressure then falls at the beginning 33 of the withdrawal of the pipette tip from the sample liquid by 0.017 V to a turning point 33b and rises until the end 34 of the withdrawal of the pipette tip from the sample liquid, in order to then fall by a small absolute value there.

FIG. 19 shows three characteristic pressure curves 9,9',9" for the sample liquid acetonitrile. The high reproducibility of the results is obvious in spite of the complex pressure curves.

FIG. 20 shows a single characteristic pressure curve 9''' for the sample liquid acetone. The pressure in the pipette, i.e., in the fluid chamber 2 and thus in the measuring chamber 3, first rises rapidly by 0.03 V from the immersion 30 and then rises constantly and steeply to a pressure elevated by approximately a further 0.023 V. At the beginning 50 of aspiration, the pressure first falls by 0.076 V and then oscillates symmetrically around a pressure higher by approximately 0.04 V, in order to then immediately rise constantly and steeply again to the value before the beginning 50 of aspiration. The rise of the pressure in each case after the immersion and the aspiration is to be attributed to the high vapor pressure of the sample liquid. In this case, the sample liquid received with the aspirate is pressed out of the pipette even before the end 51 of aspiration, followed by a bubble. The ejection of this bubble 31*c* results in a pressure drop of 0.026 V. At the end 51 of aspiration, the pressure again rises rapidly, rises further immediately after the dispensing, and again reaches the value before the beginning 50 of aspiration. A bubble is again ejected by the vapor pressure, which causes the pressure to drop, while the withdrawal of the pipette tip begins, because of which the pressure drops to the original starting pressure.

FIG. 21 shows three characteristic pressure curves 9,9',9" for the sample liquid acetone. The high reproducibility of the results is obvious in spite of the extremely complex pressure curves at least until reaching the point 51. After this, the curve 9 displays different behavior, which results from the presence of the liquid film at the outlet of the pipette tip after the withdrawal from the sample. This film closes the pipette tip in this case, so that the pressure in the interior of the pipette rises again due to the high vapor pressure of the sample liquid. Upon reaching a specific overpressure, the film breaks and releases a part of the overpressure 33*b*, in order to then form again. However, almost no sample liquid is still present in the pipette now, because of which the pressure no longer rises further. When the pipette is discarded, the pressure again falls to the starting level in this case as well.

The examples shown clearly demonstrate the reproducibility of the measurement results. All pressure changes described may be used as characterization criteria. In addition, the transient response plays a role which is not to be underestimated. Establishing tolerance limits, which are laid around the typical pressure curves, is also important. These tolerance limits may be kept very narrow thanks to the high reproducibility of the pressure curves. If the pressure curve of an unknown liquid falls in a previously established tolerance range, an assignment of this unknown sample liquid is possible in most cases.

FIGS. 22 and 23 show flow changes in the pipette of a pipetting device or pipetting system capable of performing the method according to the present invention during aspiration and dispensing of a water sample and an air sample, respectively. Flow values [φ] are shown as a function of time [t] in each case. The flow values have been normalized and are not specified in absolute numbers. The time values are specified in milliseconds.

The changes of a selected, measurable, and physically founded virtual parameter [flow] were detected in each case as a data set typical for this liquid (water) or this fluid (air). The flow value [φ] was always measured in the system liquid 11 of a pipetting device which has a basic construction corresponding to FIG. 5. The flow value or the direction and the speed of the system liquid 11 were recorded at the flow sensor. This flow sensor was situated near the pipette tip, but in an area which was always filled with system liquid. An air gap 39 separated the system liquid 11 from the aspirated or dispensed liquid (water) or from the aspirated or dispensed fluid (air).

The curves in FIGS. 22 and 23 both show a symmetrical oscillation behavior of the flow value typical for water (system liquid). This oscillation behavior is reminiscent of the pressure oscillations which were measured in the system using a water sample (cf. FIG. 10), no drift behavior of the measured values having been established here, in contrast. The two measured flow curves for water and for air are so similar that only a graphic comparison (cf. FIG. 24) or mathematical processing (cf. FIG. 25) makes clear differences visible.

FIG. 24 shows a superposition of the flow change curves of FIG. 22 "water" and FIG. 23 "air". The flow curve "air" (thick line) oscillates more rapidly and also passes into an equilibrium state more rapidly than the flow curve "water" (thin line).

FIG. 25 shows a subtraction illustration of the flow change curves FIG. 22 "water" minus FIG. 23 "air". Subtraction was selected here as the mathematical processing of the two comparison curves "water" and "air", so that an impressive differential image of the two curves is obtained. It is thus clearly shown that the different samples also cause different flow curves. It is now left to the individual user as to whether he wishes to analyze the characteristic flow curve of a sample directly and compare it to a stored flow curve of a known sample, e.g., through a superposition as in FIG. 24. Alternatively to or in combination with a direct comparison, if desired, mathematical operations as in FIG. 25, for example, may be used as an aid for comparative purposes.

Figure 26:
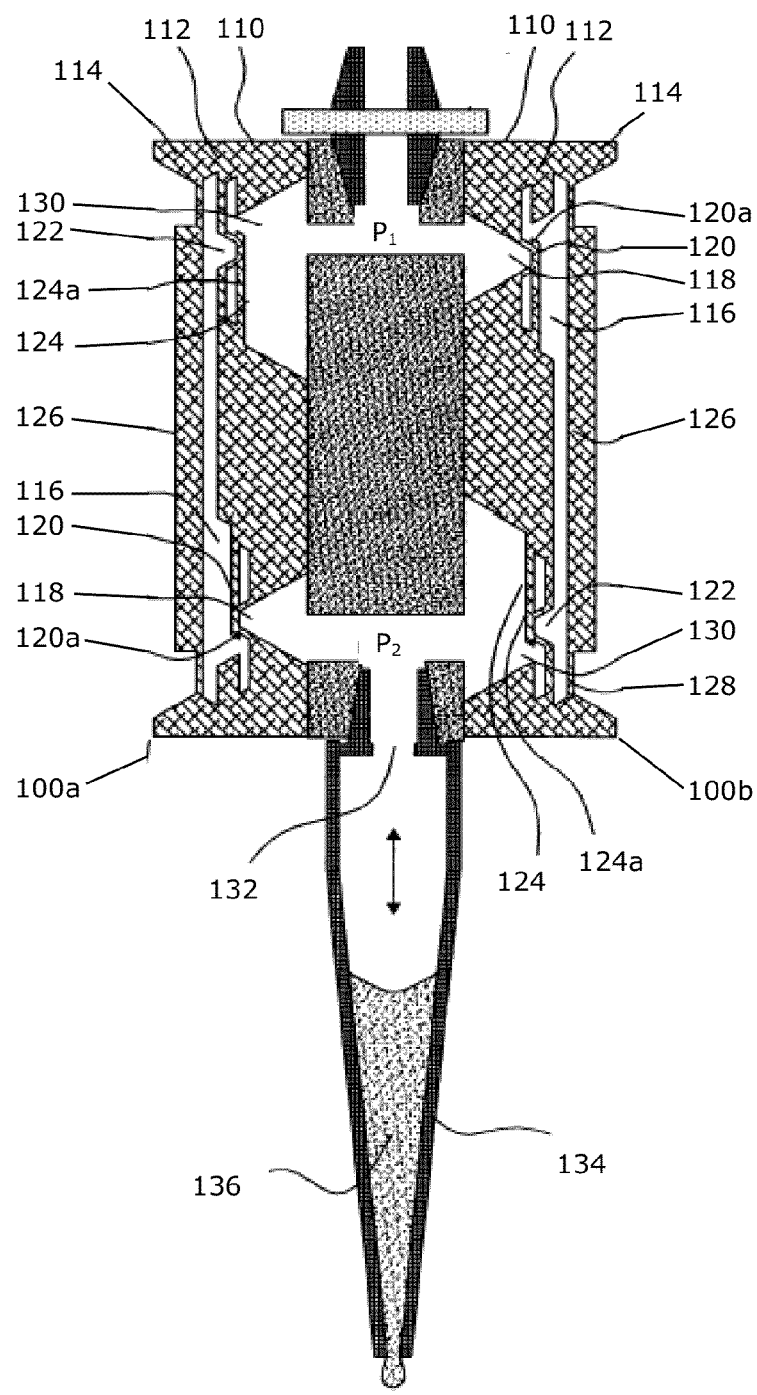
FIG. 26 shows a sectional illustration through a micro-diaphragm pump for generating a partial vacuum in the pipette tip for aspirating a liquid sample and for generating an overpressure in the pipette tip for dispensing a liquid sample.

FIG. 26 shows a sectional illustration through a microdiaphragm pump for generating a partial vacuum in the pipette tip to aspirate a liquid sample and to generate an overpressure in the pipette tip to dispense a liquid sample, which is known from FIG. 1 of DE 102 38 564 A1, which is incorporated herein in its entirety. This pipetting device known from the prior art has two micropumps having passive flap valves. This pipetting device has a first and a second micropump 110*a* and 110*b*, whose mode of operation is described in detail in DE 102 38 564 A1. Both micropumps comprise a piezoelectric actuating element 126, which is situated over a large area as a piezoelectric ceramic layer on a diaphragm 128, which is implemented as thin, and is used for reducing or enlarging the pump chamber 116. All reference numerals in FIG. 26 were taken from DE 102 38 564 A1 and are described therein.

The power consumption of this piezoelectric ceramic layer is a function of the hydrostatic pressure which the liquid to be pipetted generates in the pipette tip. However, the capillary effects occurring, the surface tension, and the vapor pressure of the liquid to be pipetted also have an effect on the power consumption of the piezoelectric ceramic layer during aspiration or dispensing of a liquid sample. Measuring and recording the course of this power consumption may therefore also be used for the characterizing of a sample liquid. As an alternative to using this known micropump, a micropump having active valves may also be used for the same purpose, as is disclosed in DE 102 38 564 A1 in connection with FIGS. 2 and 3.

The pipette tip 134 may be a steel tip or a combination of a tip adapter and a disposable pipette tip placed thereon. The micropump may (as also disclosed in DE 102 38 564 A1, the disclosure of which is incorporated herein) be used for conveying gases, such as air, but also for conveying a system liquid; this system liquid preferably being separated by an air gap from the sample liquid to be pipetted.

What is claimed is:

1. A method of selecting pipetting parameters of a pipetting device for a dispense of a specific volume of a liquid sample drawn in during aspiration, wherein the pipetting device comprises a fluid chamber which is pneumatically connected to a measuring chamber, a fluid column being situated in the fluid chamber, wherein the internal pressure of said measuring chamber is monitored using a pressure transducer, and wherein at least a first part of the fluid chamber is brought into fluid connection with a sample of the liquid by immersion of a pipette tip, the method comprising:
a) setting the fluid column into oscillation by a sudden movement in relation to the liquid sample at the beginning of the aspiration,
b) monitoring pressure with the pressure transducer in the measuring chamber, which is pneumatically connected to the fluid chamber, during the aspiration, wherein pressure changes generated during the aspiration are recorded and converted into measuring signals,
c) said measuring signals being processed by a computer or micro-processor and reproduced as a pressure curve,
d) said pressure curve being characterized by the pressure course during the transient oscillation of the fluid column at the beginning of the aspiration, and during the aspiration,
e) comparing the measured pressure curve, which is characteristic for the fluid column with the aspirated liquid sample, with known pressure curves,
f) based on the comparison of step e), selecting pipetting parameters of the pipetting device for the dispense of the specific volume of the liquid sample drawn in during the aspiration, wherein selectable pipetting parameters comprise at least a speed of a movement of a pump piston of the pipetting device, and
g) dispensing the specific volume of the liquid sample drawn in during the aspiration using the pipetting device with the selected pipetting parameters of step f).

2. The method according to claim 1, wherein in step b) the pressure is monitored and pressure changes are recorded and converted additionally upon immersion of the pipette tip into the sample of the liquid.

3. The method according to claim 1, wherein the fluid chamber comprises a pipette tip of a pipetting device for liquid handling of samples, in which a partial vacuum is generated for aspirating to generate pressure changes in the fluid column.

4. The method according to claim 1, wherein the pressure curve is displayed on a display screen or printed and visually compared to known pressure curves, which are displayed on the display screen or printed.

5. The method according to claim 1, wherein the pressure curve is analyzed on the basis of an algorithm and mathematically compared to known and correspondingly analyzed pressure curves.

6. The method according to claim 5, wherein the pressure curve is automatically compared and—if its course lies within established tolerances—corresponding pipetting parameters of known liquids are selected for the dispense of the specific volume of the liquid sample drawn in during aspiration.

7. The method according to claim 5, wherein the pressure curve is automatically compared and—if its course lies outside established tolerances—new pipetting parameters are assigned to the liquid sample drawn in during aspiration and displayed to an operator.

8. The method according to claim 6, wherein the tolerances are established before or after the reproduction of the pressure curve, but prior to dispensing the liquid.

9. A method of selecting pipetting parameters of a pipetting device for a dispense of a specific volume of a liquid sample drawn in during aspiration, wherein the pipetting device comprises a fluid chamber with a fluid column being situated in the fluid chamber, wherein the internal pressure of said fluid chamber is monitored using a pressure transducer, and wherein at least a first part of the fluid chamber is brought into fluid connection with a sample of the liquid by immersion of a pipette tip, the method comprising:
a) setting the fluid column into oscillation by a sudden movement in relation to the liquid sample at the beginning of the aspiration,
b) monitoring pressure with the pressure transducer in the fluid chamber during the aspiration, wherein pressure changes generated during the aspiration are recorded and converted into measuring signals,
c) said measuring signals being processed by a computer or micro-processor and reproduced as a pressure curve,
d) said pressure curve being characterized by the pressure course during the transient oscillation of the fluid column at the beginning of the aspiration, and during the aspiration,
e) comparing the measured pressure curve, which is characteristic for the fluid column with the aspirated liquid sample, with known pressure curves,
f) based on the comparison of step e), selecting pipetting parameters of the pipetting device for the dispense of the specific volume of the liquid sample drawn in during the aspiration, wherein selectable pipetting parameters comprise at least a speed of a movement of a pump piston of the pipetting device, and
g) dispensing the specific volume of the liquid sample drawn in during the aspiration using the pipetting device with the selected pipetting parameters of step f).

10. The method according to claim 9, wherein in step b) the pressure is monitored and pressure changes are recorded and converted upon immersion of the pipette tip into the sample of the liquid.

11. The method according to claim 9, wherein the fluid chamber comprises a pipette tip of a pipetting device for liquid handling of samples, in which a partial vacuum is generated for aspirating to generate pressure changes in the fluid column.

12. The method according to claim 9, wherein the pressure curve is displayed on a display screen or printed and visually compared to known pressure curves, which are displayed on the display screen or printed.

13. The method according to claim 9, wherein the pressure curve is analyzed on the basis of an algorithm and mathematically compared to known and correspondingly analyzed pressure curves.

14. The method according to claim 13, wherein the pressure curve is automatically compared and—if its course lies within established tolerances—corresponding pipetting parameters of known liquids are selected for the dispense of the specific volume of the liquid sample drawn in during aspiration.

15. The method according to claim 13, wherein the pressure curve is automatically compared and—if its course lies outside established tolerances—new pipetting parameters are assigned to the liquid sample drawn in during aspiration and displayed to an operator.

16. The method according to claim 14, wherein the tolerances are established before or after the reproduction of the pressure curve, but prior to dispensing the liquid.

17. A method of selecting pipetting parameters of a pipetting device for pipetting a specific volume of a liquid sample, said pipetting comprising aspiration and dispense of liquid volumes, wherein the pipetting device comprises a fluid chamber with a fluid column being situated in the fluid chamber, wherein the internal pressure of said fluid chamber is monitored using a pressure transducer, and wherein at least a first part of the fluid chamber is brought into fluid connection with a sample of the liquid by immersion of a pipette tip, the method comprising:

a) aspirating a volume of a liquid sample,
b) setting the system liquid fluid column into oscillation by a sudden movement in relation to the liquid sample at the beginning of the aspiration,
c) monitoring pressure with the pressure transducer in the fluid chamber during the aspiration, wherein pressure changes generated during the aspiration are recorded and converted into measuring signals,
d) said measuring signals being processed by a computer or micro-processor and reproduced as a pressure curve,
e) said pressure curve being characterized by the pressure course during the transient oscillation of the fluid column at the beginning of the aspiration, and during aspiration,
f) comparing the measured pressure curve, which is characteristic for the fluid column with the aspirated liquid sample, with known pressure curves,
g) based on the comparison of step f), selecting pipetting parameters of the pipetting device for the dispense of the specific volume of the liquid sample drawn in during the aspiration, wherein selectable pipetting parameters comprise at least a speed of a movement of a pump piston of the pipetting device, and
h) pipetting at least one specific volume of the liquid sample used for the steps a)-e) using the pipetting device with the selected pipetting parameters of step g).

18. The method according to claim 17, wherein in step c) the pressure is monitored and pressure changes are recorded and converted additionally upon immersion of the pipette tip into the sample of the liquid.

19. The method according to claim 17, wherein the fluid chamber comprises a pipette tip of a pipetting device for liquid handling of samples, in which a partial vacuum is generated for aspirating to generate pressure changes in the fluid column.

20. The method according to claim 17, wherein the pressure curve is displayed on a display screen or printed and visually compared to known pressure curves, which are displayed on the display screen or printed.

21. The method according to claim 17, wherein the pressure curve is analyzed on the basis of an algorithm and mathematically compared to known and correspondingly analyzed pressure curves.

22. The method according to claim 21, wherein the pressure curve is automatically compared and—if its course lies within established tolerances—corresponding pipetting parameters of known liquids are selected for pipetting of at least one specific volume of the liquid sample.

23. The method according to claim 21, wherein the pressure curve is automatically compared and—if its course lies outside established tolerances—new pipetting parameters are assigned to the liquid sample used for the steps a)-e) and displayed to an operator.

24. The method according to claim 22, wherein the tolerances are established before or after the reproduction of the pressure curve, but prior to pipetting the liquid.

* * * * *